United States Patent [19]
Gordon

[11] Patent Number: 5,549,680
[45] Date of Patent: Aug. 27, 1996

[54] APPARATUS FOR TOTAL TEMPOROMANDIBULAR JOINT REPLACEMENT

[75] Inventor: Jeffrey D. Gordon, Claypool, Ind.

[73] Assignee: Biomet, Inc., Warsaw, Ind.

[21] Appl. No.: 194,543

[22] Filed: Feb. 10, 1994

[51] Int. Cl.$^6$ ............................................. A61F 2/30
[52] U.S. Cl. ........................ 623/18; 623/11; 623/16
[58] Field of Search .............................. 623/11, 16, 18, 623/23–23, 66

[56] References Cited

U.S. PATENT DOCUMENTS

| | | |
|---|---|---|
| D. 248,665 | 7/1978 | Homsy et al. . |
| D. 277,981 | 3/1985 | Homsy et al. . |
| D. 288,236 | 2/1987 | Homsy et al. . |
| D. 288,237 | 2/1987 | Homsy et al. . |
| D. 288,238 | 2/1987 | Homsy et al. . |
| D. 295,076 | 4/1988 | Homsy et al. . |
| 3,178,728 | 4/1965 | Christensen . |
| 3,488,779 | 1/1970 | Christensen . |
| 3,579,643 | 5/1971 | Morgan . |
| 3,889,300 | 6/1975 | Smith . |
| 4,156,296 | 5/1979 | Johnson et al. . |
| 4,231,121 | 11/1980 | Lewis . |
| 4,693,722 | 9/1987 | Wall . |
| 4,726,808 | 2/1988 | Collins . |
| 4,778,472 | 10/1988 | Homsy et al. . |
| 4,917,701 | 4/1990 | Morgan . |
| 4,936,852 | 6/1990 | Kent et al. . |
| 5,129,903 | 7/1992 | Luhr et al. . |
| 5,383,936 | 1/1995 | Kubein-Meesenburg .................. 623/18 |
| 5,405,393 | 4/1995 | Falkenström ............................. 623/18 |

FOREIGN PATENT DOCUMENTS 1332071  10/1973  United Kingdom ...................... 623/18

OTHER PUBLICATIONS

G. J. Pruim, H. J. DeJongh and J. J. Ten Bosch, "Forces Acting on the Mandible During Bilateral Static Bite at Different Bite Force Levels", *Biomechanics* vol. 13, pp. 775–763, 1980.

G. J. Pruim, J. J. Ten Bosch and H. J. DeJongh, "Jaw Muscle EMG–Activity and Static Loading of the Mandible", i Biomechanics vol. 11, pp. 389–395, 1978.

Proceedings from symposium entitled "Current Concepts of TMJ Total Joint Replacement," University of Medicine & Denistry of New Jersey, Mar. 20 & 21, 1992.

*Primary Examiner*—David H. Willse
*Assistant Examiner*—P. Zuttarelli
*Attorney, Agent, or Firm*—Harness, Dickey & Pierce, P.L.C.

[57] ABSTRACT

A biocompatible prosthetic device for the replacement of the temporomandibular joint is provided. The prosthetic device includes an artificial condylar component having a substantially spherical convex articular surface of a first spherical radius for replacing the articular surface of the condylar head. The prosthetic device further includes artificial mandibular fossa component having a substantially spherical concave articular surface of a second spherical radius greater than the first spherical radius. The present invention further includes a surgical method for installation of this prosthetic device.

18 Claims, 5 Drawing Sheets

5,549,680

APPARATUS FOR TOTAL TEMPOROMANDIBULAR JOINT REPLACEMENT

BACKGROUND OF THE INVENTION

This invention relates generally to medical implant devices, and more particularly to a biocompatible prosthetic device for the replacement of the mandibular condyle and the mandibular fossa which together form the temporomandibular joint.

A variety of medical conditions in the area of the temporomandibular joint can result in the need for partial or total replacement of this joint. Some of the conditions which may require such a surgical procedure include cases of osteoarthritis, rheumatoid arthritis, traumatic arthritis, malignancy, benign neoplasms, functional deformity, failed total temporomandibular joint arthroplasty, avascular necrosis and ankylosis.

In these types of situations, bone degradation may occur on one or both sides of the temporomandibular joint, namely, in the mandibular fossa region or in the opposing mandibular condyle. Where both the mandibular fossa and the mandibular condyle are degraded through one or more of the above or other conditions, a total temporomandibular joint (hereinafter "TMJ") replacement procedure may be desirable to replace the affected bone portions with prosthetic implant devices.

The natural movement of the temporomandibular joint allows for two distinct movements of the mandible relative to the maxilla. The first movement produces hinging motion in one plane consistent with a ginglymoid joint. The second movement is gliding motion consistent with a arthrodial joint. These movements classify the temporomandibular joint as a ginglymoarthrodial joint. These two motions are created by the involvement of the muscles of mastication, primarily the masseter, temporalis, and pterygoid muscles. As such, the human jaw is able to accomplish circular chewing in at least a limited fashion by combining these distinctive movements.

Prior attempts to reconstruct one or both portions of the temporomandibular joint have encountered several disadvantages. Firstly, some temporomandibular joint implant devices have failed to allow for the limited circular pivoting movement such as that accomplished naturally by the human jaw. In addition, in the case of implant surgery occurring on only one side of the jaw, the range of movement of the replacement joint may not match the range of movement of the remaining natural joint. The range of movement of the jaw as a whole is then largely limited by the artificial side, in the case where the range of movement of the artificial side is less than that of the remaining natural joint.

The natural anatomical shape of the mandibular fossa is an oblong shape, which shape has been duplicated by prior temporomandibular joint implant devices. Prior implant devices have also included the use of oblong shaped condylar head portions for engaging the mandibular fossa. The use of these shapes for temporomandibular joint implant devices, however, resulted in the need for critical placement of both the artificial mandibular fossa component, upon the zygomatic arch, and the artificial condyle upon the ramus relative to each other. As such, the use of oblong shapes for artificial mandibular fossa components and/or artificial condyles may require repeated minute adjustments in these components, which may even include bending these components. This is undesirable both in the extended time period required for accomplishing the surgical procedure, as well as in the possible damage to the prosthetic device components resulting from their manipulation and/or bending during the procedure.

Another disadvantage of prior temporomandibular joint implant devices is that many of these devices are attached upon the present anatomical structure of the region. This is disadvantageous because it increases the change in relative pivoting position and relative jaw position more than is necessary away from the natural position.

A need therefore exists for a biocompatible prosthetic device for the total replacement of the temporomandibular joint which is designed to function most similar to the natural function of the human jaw. A need also exists for such a device to be easily and quickly inserted and adjusted in proper alignment by the surgeon. A need further exists for such a device to allow circular chewing movement, with a minimum of deviation from the natural motion of the mandible and maxilla.

SUMMARY OF THE INVENTION

An advantage of the present invention is to provide a biocompatible prosthesis implant device for the total replacement of the temporomandibular joint which most nearly represents the original, natural circular movement of the human jaw.

Another advantage of the present invention is to provide a biocompatible prosthesis implant device that is easy for a surgeon to install and adjust quickly.

A further advantage of the present invention is to provide a biocompatible prosthesis implant device for the total replacement of the temporomandibular joint that is positioned to most accurately represent the physiologic motion of the human jaw.

The present invention, in one form thereof, provides a biocompatible prosthetic implant device for the total replacement of the temporomandibular joint. The device includes a plate operable for being enhanced in a secured relation with the ramus, means for fastening the plate to the ramus, and means attached to the plate for providing a substantially spherical convex articular surface of a first spherical radius for replacing the articular surface of the condylar head. The device further includes means for providing a substantially spherical concave articular surface of a second spherical radius which is greater than the first spherical radius by a preselected amount for replacing the articular surface of the mandibular fossa. The device also includes means for fastening the means for providing a substantially spherical concave articular surface to the zygomatic arch.

BRIEF DESCRIPTION OF THE DRAWINGS

Other advantages of the present invention will become apparent to one skilled in the art upon reading the following specification and the following drawings.

DETAILED DESCRIPTION OF THE PREFERRED EMBODIMENT

It should be understood that while this invention is described in connection with a particular example, the scope of the invention need not be so limited. Rather, those skilled in the art will appreciate that the following teachings can be used in a much wider variety of applications than the examples specifically mentioned herein.

Figure 1:
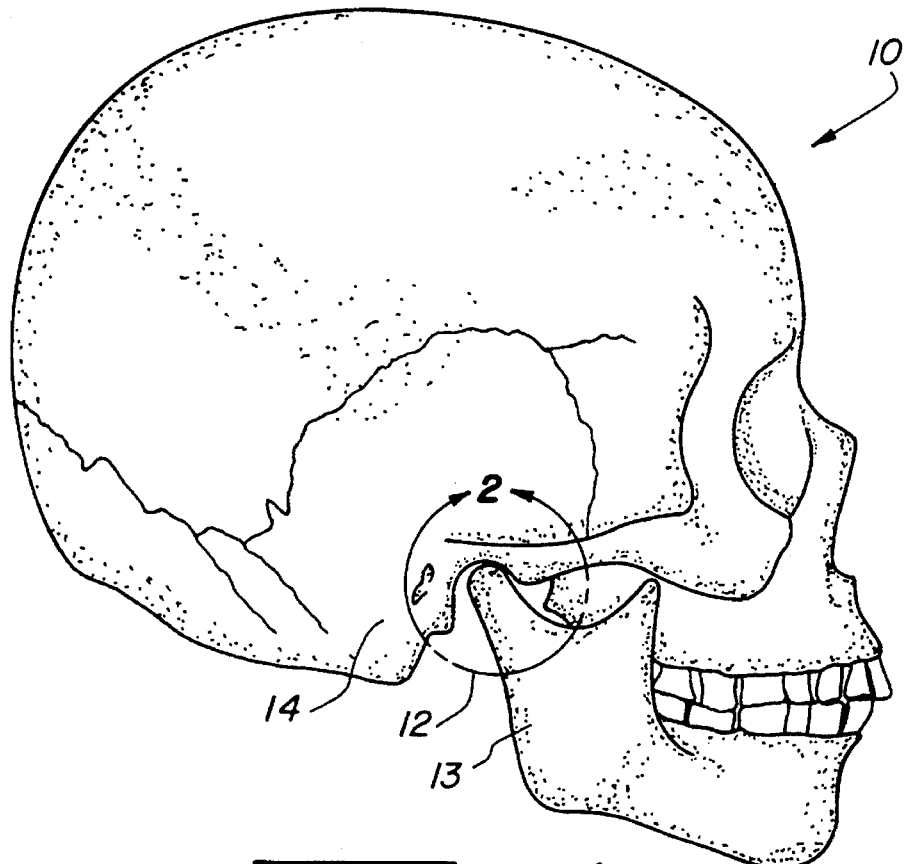
FIG. 1 is a side view of a human skull illustrating the natural environment of a temporomandibular joint.

Referring now to FIG. 1, there is shown a side view of a human skull 10 illustrating the natural environment of a temporomandibular joint region 12. The temporomandibular joint region 12 is shown in enlarged fashion in FIG. 2 as including a mandible 13 and a temporal bone 14. The mandible 13 includes a condyle 15 which is a natural protrusion of the ramus 16. The condyle 15 is further shown to include an articular surface 18, which is naturally of a generally rounded convex configuration. The temporomandibular joint region 12 also includes a mandibular fossa 20 which is a region adjoining the zygomatic arch 22. The mandibular fossa 20 includes an articular surface 24 which is of a generally rounded concave configuration.

Figure 3:
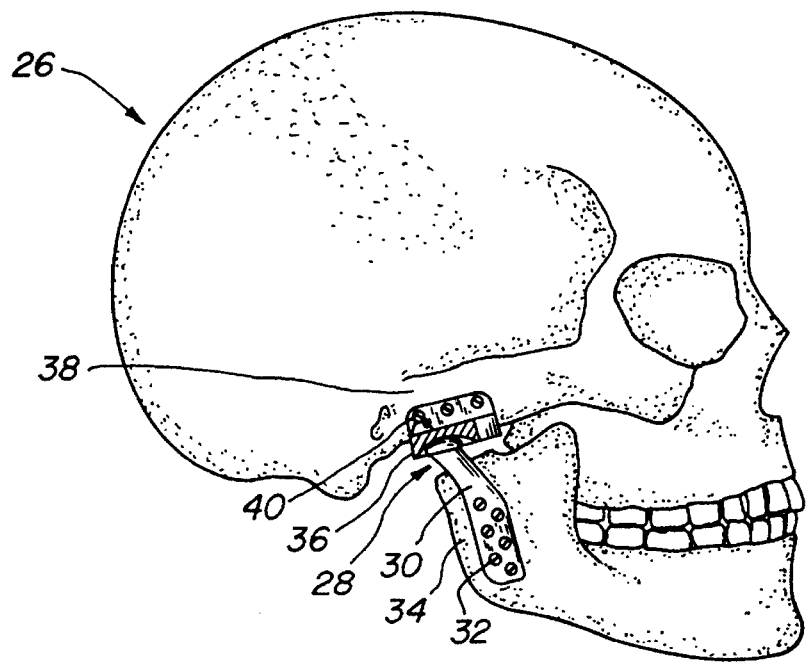
FIG. 3 is a side view of a human skull illustrating the environment of a prosthetic device for the total replacement of the temporomandibular joint.

Referring now to FIG. 3, there is shown a side view of a human skull 26 illustrating the environment of a biocompatible prosthetic device 28 for the replacement of the temporomandibular joint. The prosthetic device 28 is operable to allow physiological movement of the mandible relative to the maxilla. In this regard, the mandible is not only able to move in a hinging motion, but it is also able to be protruded in the forward direction and retracted in the backward direction by virtue of the range of movement provided by the masseter, temporalis, and pterygoid muscles. In addition, in the case of implant surgery on only one side of the jaw, the range of movement of the prosthetic device 28 is able to approximate that range of movement of the remaining natural joint. Furthermore, the artificial condyles of the prosthetic device 28 do not require extensive repeated adjustments of the various components during implantation. Finally, the prosthetic device 28 is better able to approximate the natural pivot location between the components of the natural jaw as well as the approximate relative position between the components of the natural jaw.

Figure 2:
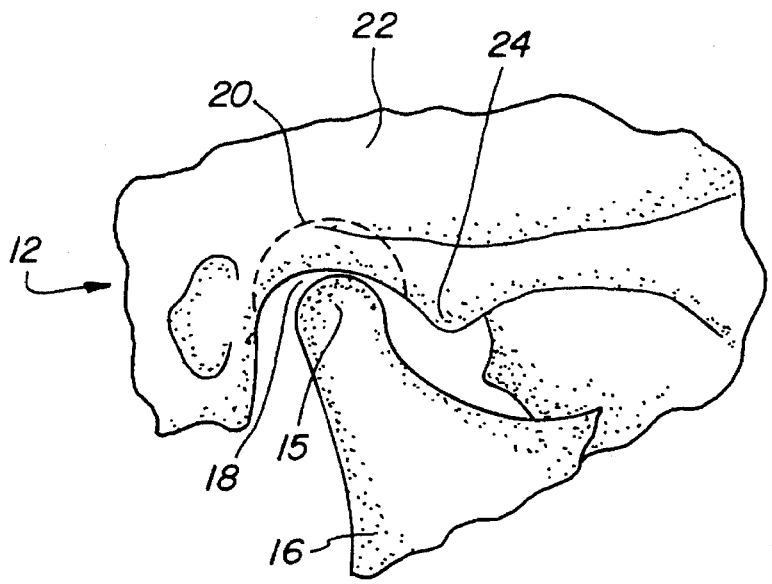
FIG. 2 is an enlarged side view illustrating the temporomandibular joint region shown in FIG. 1.

The prosthetic device 28 will now be described in greater detail. The prosthetic device 28 includes means for providing a substantially spherical convex articular surface of a first spherical radius for replacing the articular surface 18 of the condyle 15 as shown in FIG. 2. In a preferred embodiment, this is provided as an artificial condyle component 30. The prosthetic device 28 also includes means for fastening the means for providing a substantially spherical convex articular surface to the ramus. In a preferred embodiment, this is provided by a plurality of condyle fasteners 32 which are operable to enhance a secured relation between the artificial condyle component 30 and the ramus 34. As such, the artificial condyle component 30 is attached to the ramus 34 to act as a replacement condyle once the natural condyle has been removed.

The prosthetic device 28 is further shown to include means for providing a substantially spherical concave articular surface of a second spherical radius for replacing the articular surface of the mandibular fossa. In a preferred embodiment, this is provided as an artificial mandibular fossa component 36. The prosthetic device 28 further includes means for fastening the means for providing a substantially spherical concave articular surface to the zygomatic arch 38. In a preferred embodiment, this is provided as a plurality of fasteners 40 which are disposed in an engaging relation to enhance a substantially secured relation between the artificial mandibular fossa component 36 and the zygomatic arch 38.

Both the condyle fasteners 32 and the mandibular fossa fasteners 40 are preferably surgical fasteners of a type well known to those skilled in the art. As such, they may be in the form of self-tapping bone screws constructed of a material selected from the group consisting of commercially pure titanium, titanium alloys and Ti—6Al—4V. Each bone screw typically has a minor diameter represented by the width of the insertable portion of the screw excluding that resulting from the horizontal extension of the screw threads, and a major diameter represented by the total width of the insertable portion of the screw, including the threads. Typical diameters of bone screws used in the present invention are 2.7 mm, 3.2 mm, 2.0 mm, and 2.3 mm. The condyle fasteners 32 and the mandibular fossa fasteners 40 are preferably selected to be of a length suitable for engaging a substantial depth of the ramus 34 or the zygomatic arch 38 into which they may be threadably inserted. Preferably, the heads of these bone screws have a contoured undersurface shaped to match a corresponding countersink contour, or alternatively have a substantially flat undersurface when secured flush against a flat surface.

Figure 4:
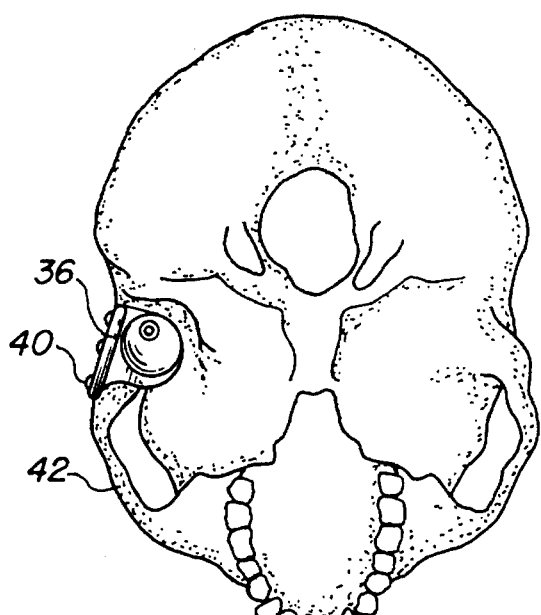
FIG. 4 is a bottom view of a human maxilla illustrating an artificial mandibular fossa component of a prosthetic device for the total replacement of a temporomandibular joint.
Figure 5:
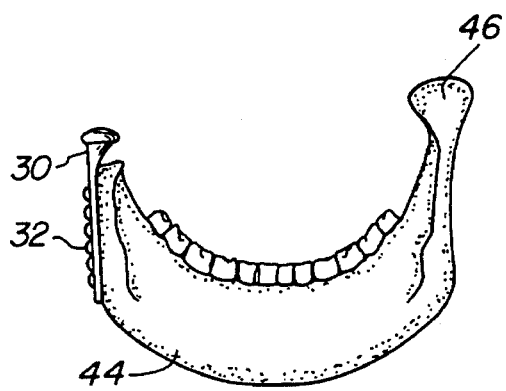
FIG. 5 is a posterior-to-anterior view of a human mandible illustrating the environment of a natural condyle and an artificial condyle component of a prosthetic device for the total replacement of a temporomandibular joint.

Once the artificial condyle component 30 and the artificial mandibular fossa component 36 are placed in a substantially secured relation with the ramus 34 and the zygomatic arch 38, respectively, they are operable to be disposed in a three-dimensional relatively rotatable engagement. The relative positions of the artificial condyle component 30 and the artificial mandibular fossa component 36 are illustrated in expanded fashion in FIGS. 4 and 5. FIG. 4 shows a bottom view of a human maxilla 42 including the artificial mandibular fossa component 36. FIG. 5 shows a posterior-to-anterior view of a human mandible 44 illustrating a natural condyle 46 and an artificial condyle component 30 of the prosthetic device of the present invention.

Figure 6:
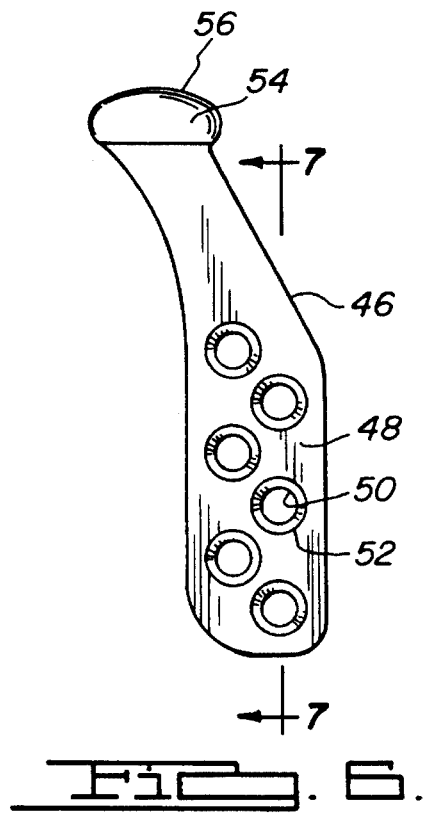
FIG. 6 is a side view illustrating an artificial condyle component according to the teachings of a preferred embodiment of the present invention.

The preferred embodiment of the artificial condyle component 30 is shown now with reference to FIG. 6, which is a side view according to the teachings of a preferred embodiment of the present invention. The artificial condyle component 30 is shown to include a plate 48 which is of a substantially flattened configuration. The plate 48 is preferably constructed from a cobalt chrome alloy, although it will be appreciated that other suitable materials may be used. The plate 48 is preferably constructed to a suitable low-profile configuration so that when it is installed upon the ramus, its protrusion above the bone surface is minimized. This low-profile configuration enhances the cosmetic appearance by minimized protrusion as observed above the skin following the replacement surgery. Preferably, the plate 48 has a thickness of about 0.080 inch, although it will be appreciated that other suitable thicknesses may be used. The artificial condyle component 30 may also include a porous titanium or other bone ingrowth-enhancing coating (not shown) on a surface operable for contacting the ramus.

The plate 48 is also shown to include a plurality of condylar fastener openings 50 disposed therethrough. The condylar fastener openings 50 are operable for allowing the traverse of a plurality of condyle fasteners, such as those shown at 32 in FIG. 3, for enhancing a secured relation between the plate 48 and the underlying ramus, which in turn enhances a secured relation of the artificial condyle component 30 as a whole relative to the ramus. Preferably, from five to eight condylar fastener openings 50 are suitable for accomplishing this task, although it will be appreciated that any suitable number of openings may be used.

Preferably, the condylar fastener openings 50 are arranged in a staggered pattern arrangement upon the plate 48. It will be appreciated, however, that any suitable arrangement for the condylar fastener openings 50 may be used. The condylar fastener openings 50 are each shown to be provided with a countersink 52 for accepting at least part of a correspondingly shaped head of a surgical fastener. Each countersink 52 is thus operable for enhancing a low profile arrangement for the plate 48 in its installed position by reducing the distance from which surgical fasteners are able to protrude from within the condylar fastener openings 50 above the surface of the plate 48.

The artificial condyle component 30 is further shown to include a condylar head 54 which is operable to include a substantially spherical convex articular surface 56 of a preselected first spherical radius of preferably greater than about 0.200 inches to provide uniform surface contact to reduce contact stresses. The articular surface 56 is operable to engage in a three-dimensional relatively rotatable fashion a corresponding articular surface of an artificial mandibular fossa component as will be described below. This arrangement provides the artificial condyle component 30 with the ability to approximate the physiologic movement of the human jaw with respect to vertical movement as well as forward protrusion and retraction. The posterior transition from the plate 30 to the articular surface 56 preferably does not include a lip which would otherwise interfere with the mandibular fossa component 36 in the event that a dislocation should occur. Accordingly, the absence of such a lip permits closed reduction should a dislocation occur. Both the condylar head 54 and its articular surface 56 may preferably be constructed from a cobalt chrome alloy. It will be appreciated, however, that other suitable materials may be used.

Figure 8:
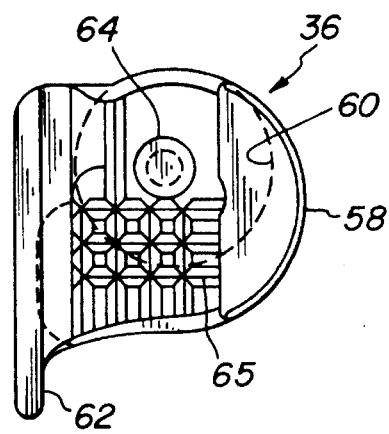
FIG. 8 is a top view illustrating an artificial mandibular fossa component according to the teachings of a preferred embodiment of the present invention.
Figure 9:
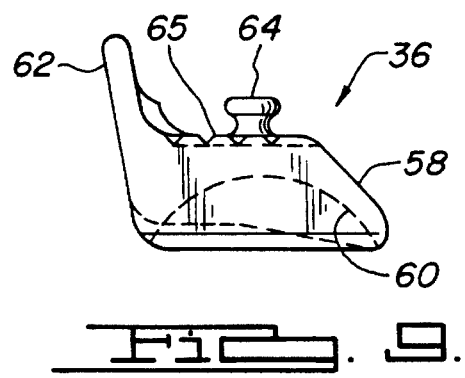
FIG. 9 is an end view illustrating the artificial mandibular fossa component shown in FIG. 8.
Figure 10:
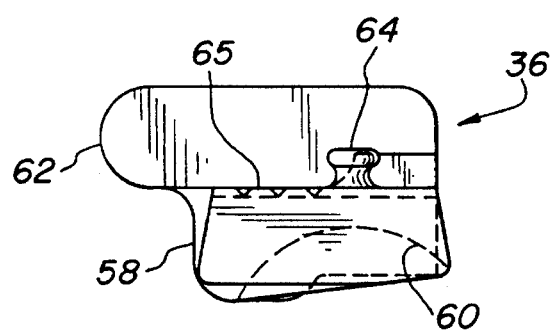
FIG. 10 is a side view illustrating the artificial mandibular fossa component shown in FIG. 8.

The artificial mandibular fossa component 36 shown in FIG. 3 is now described in greater detail. FIGS. 8, 9 and 10 show a top view, an end view and a side view, respectively, of the artificial mandibular fossa component 36 according to the teachings of a preferred embodiment of the present invention. The artificial mandibular fossa component 36 includes a concave articular surface that is operable for engaging a corresponding convex articular surface of the artificial condyle component 30 previously described. In this arrangement, the artificial mandibular fossa component 36 is also able to enhance the relative physiologic circular movement described before, especially with regard to vertical movement, forward protrusion and retraction. The artificial mandibular fossa component 36 includes a main body 58 upon the lower surface of which is disposed a concave articular surface 60 that is operable for engaging in a three-dimensional relatively rotatable fashion the substantially spherical convex articular surface 56 of the corresponding artificial condyle component 30. The main body 58 may preferably be constructed from a material selected from the group consisting of ultra high molecular weight polyethylene and cobalt chrome alloys. It will be appreciated, however, that any suitable material may be used.

The concave articular surface 60 is constructed to be of a preselected second spherical radius which is greater than the first spherical radius of the convex articular surface 56 by a preselected amount. Preferably, the second spherical radius of the concave articular surface 60 is greater than at least 5%, and more preferably greater than from about 5% to about 35%, the first spherical radius of the convex articular surface 56. This experimentally-determined relative radius range between the convex articular surface 56 and the concave articular surface 60 is most important to the present invention because it has been determined that this range of mismatched relative radii allow the convex articular surface 56 to move most favorably in a three-dimensional relatively rotatable fashion when engaged against the concave articular surface 60, in terms of freedom of movement and reduced contact stresses of engagement surfaces.

The artificial mandibular fossa component 36 is further shown to include a flange 62 which protrudes from the main body 58. The flange 62 is operable to provide a surface for attachment of the artificial mandibular fossa component 36 to the zygomatic arch. Preferably, the flange 62 is constructed of a material that allows for the formation of a plurality of fastener openings therewithin by a surgeon during a surgical procedure. These fastener openings must be operable for retaining a plurality of surgical fasteners, such as those described above, for retaining the flange 62, and the artificial mandibular fossa component 36, in a substantially secured relation upon the zygomatic arch. As such, it is preferred that the flange 62 be constructed from an ultra high molecular weight polyethylene material, although it will be appreciated that other suitable materials may be used.

The ability of the flange 62 to have fastener openings formed therein enhances the strength of its attachment to the zygomatic arch because it allows for placement of precisely located fastener openings in the flange 62. This is advantageous because the configuration of the zygomatic arch may result in the need for fasteners to be located at specific locations along its surface if an artificial mandibular fossa component is to be successfully retained thereupon.

Figure 7:
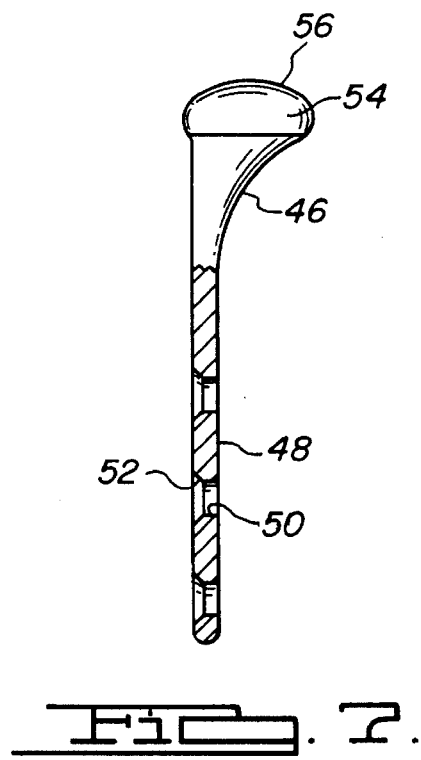
FIG. 7 is an end view of the artificial condyle component shown in FIG. 6.

In a preferred embodiment, the flange 62 is formed as an integral extension of the main body 58, and as such, the main body 58 and the flange 62 are constructed of the same material. Alternatively, it will be appreciated that the flange 62 may also be provided with a plurality of fastener openings (not shown) of similar configuration to the condylar fastener openings illustrated at 50 in connection with FIGS. 6 and 7.

It will be appreciated that the flange 62 may be operable to allow the creation of fastener openings thereupon of more than one size. In such an arrangement, the differently sized openings are suitable for accommodating the insertion of differently sized surgical fasteners. For example, the surface configuration of the underlying zygomatic arch to which the flange 62 is attached may cause the use of differently sized surgical fasteners to be most beneficial.

The flange 62 may also include a porous titanium or other bone ingrowth-enhancing coating (not shown) on a surface operable for contacting the zygomatic arch. This coating is typically applied in a thin layer upon the expected contacting surface through such methods as a plasma spray technique.

The artificial mandibular fossa component 36 is also shown to include a tab 64 which is a projection above the upper surface of the main body 58. The tab 64 is useful in providing increased surface area in dimensions different from the single plane otherwise formed by the upper surface of the main body 58. As such, the tab 64 is operable for providing increased surface area upon which an adhesive, such as polymethyl methacrylate (PMMA) bone cement, may adhere in bonding the artificial mandibular fossa component 36 into the mandibular fossa before securing this component further by surgical fasteners to the zygomatic arch.

The artificial mandibular fossa component 36 may also be provided with a plurality of surface corrugations 65 which are preferably of the type shown in FIGS. 8, 9 and 10. It will be appreciated, however, that the surface corrugations 65 may be of any suitable shape that is operable for increasing the surface area to which an adhesive may adhere, and may also be operable for enhancing a stationary engagement between the artificial mandibular fossa component 36 and the zygomatic arch.

Figures 11, 12:
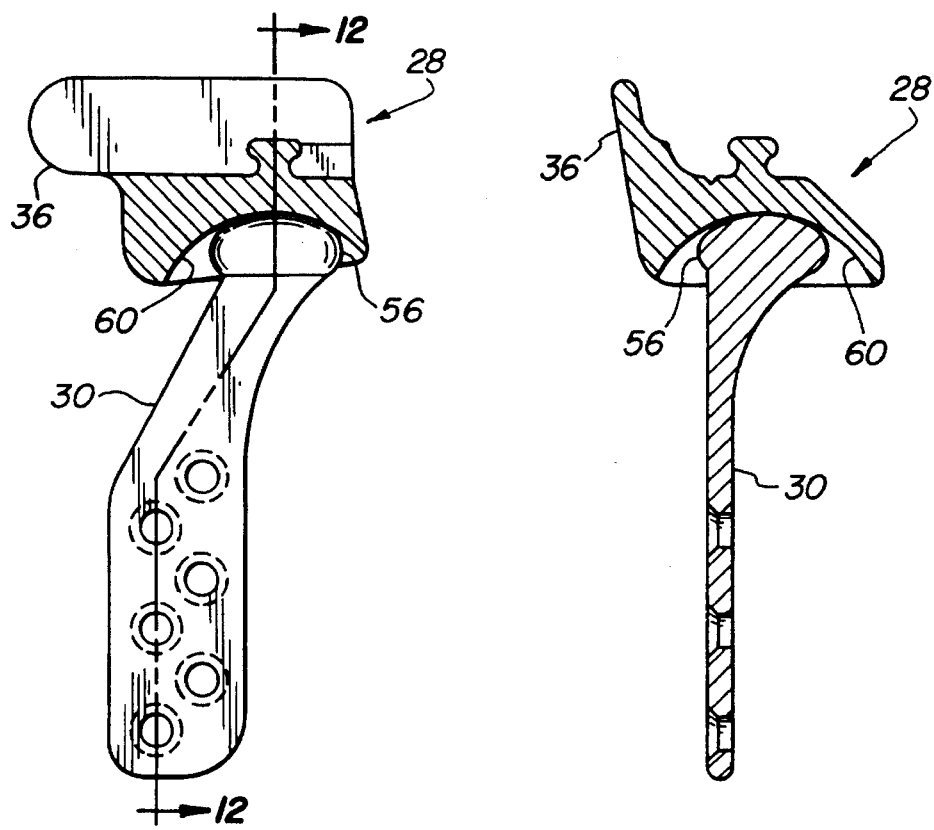
FIG. 11 is a partial cross-sectional side view illustrating an artificial condyle component in conjunction with an artificial mandibular fossa component according to the teachings of a preferred embodiment of the present invention.
FIG. 12 is a cross-sectional end view illustrating the artificial condyle component and artificial mandibular fossa component assembly illustrated in FIG. 11.

Referring now to FIGS. 11 and 12, the biocompatible prosthetic device 28 according to the teachings of a preferred embodiment of the present invention is shown in assembled form. The prosthetic device 28 is shown to include the artificial condyle component 30 and the artificial mandibular fossa component 36 as previously described. The artificial condyle component 30 and the artificial mandibular fossa component 36 are operable to be engaged in a three-dimensional relatively rotatable engagement of the convex articular surface 56 with the concave articular surface 60, so as to approximate the physiologic movement of the human temporomandibular joint when installed.

Figures 13, 14:
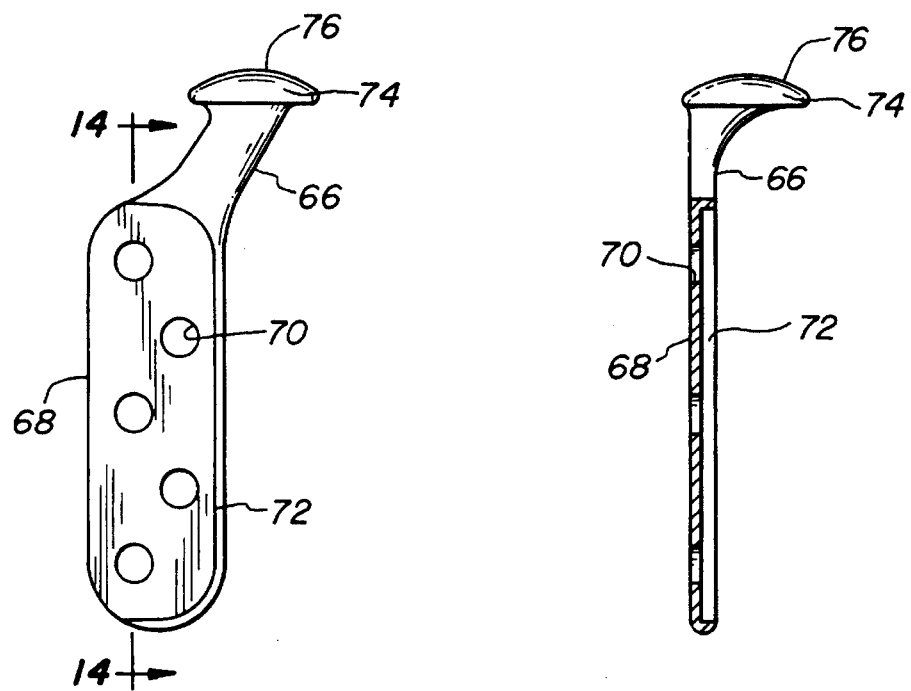
FIG. 13 is a side view illustrating an artificial condyle component according to the teachings of a second preferred embodiment of the present invention.
FIG. 14 is an end view of the artificial condyle component shown in FIG. 13.

An alternative embodiment of an artificial condyle component will now be described with reference to FIGS. 13 and 14. The artificial condyle component 66 according to this alternative embodiment is similar in construction to the artificial condyle component 30 previously described. In this regard, the artificial condyle component 66 includes a plate 68 which is of a substantially flat configuration. The plate 68 includes a plurality of condylar fastener openings 70 which are shown as five openings in FIG. 13. As before, these openings may be arranged in any suitable number and configuration. The plate 68 also includes a reinforcing flange 72 which serves to enhance the structural rigidity of the artificial condyle component 66. In addition, the artificial condyle component 66 also includes a condylar head 74 which includes an articular surface 76 that is preferably of a substantially spherical convex configuration having a preselected first spherical radius.

The artificial condyle component 66 may be constructed of the same or different materials as the artificial condyle component 30 previously mentioned. Also, the artificial condyle component 66 may selectively incorporate any of the features mentioned above with respect to the artificial condyle component 30.

Figure 15:
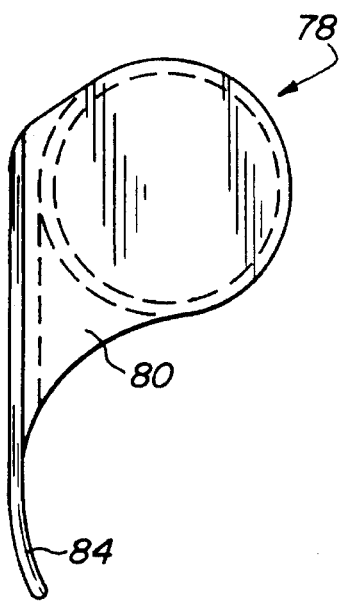
FIG. 15 is a top view illustrating an artificial mandibular fossa component according to the teachings of a second preferred embodiment of the present invention.
Figure 16:
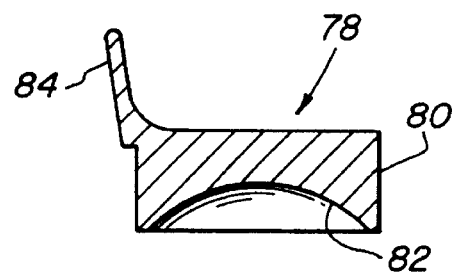
FIG. 16 is an end view illustrating the artificial mandibular fossa component shown in FIG. 15.
Figure 17:
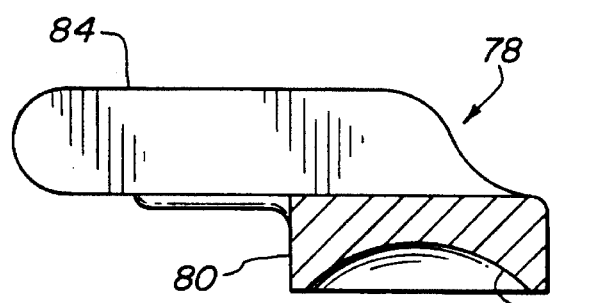
FIG. 17 is a side view illustrating the artificial mandibular fossa component shown in FIG. 15.

An alternative embodiment of artificial mandibular fossa component will now be described with reference to FIGS. 15, 16 and 17. The artificial mandibular fossa component 78 according to this embodiment includes a main body 80 in similar fashion as the artificial mandibular fossa component 36 described previously. Disposed upon the main body 80 is an articular surface 82, which is a concave surface of a preselected second spherical radius. The second spherical radius of the concave articular surface 80 is about 5% or greater than the spherical radius of the convex articular surface 76, and preferably from about 5% to about 35% greater than the first spherical radius of the convex articular surface 76. The convex articular surface 76 and the concave articular surface 82 are intended to engage in a three-dimensional relatively rotatable fashion, so as to approximate the physiologic movement of the human jaw. The artificial mandibular fossa component 78 further includes a flange 84 which is disposed as a projection from the main body 80, in similar fashion as before. The artificial mandibular fossa component 78 may be constructed from the same or other materials as those previously described with respect to the artificial mandibular fossa component 36.

Figure 18:
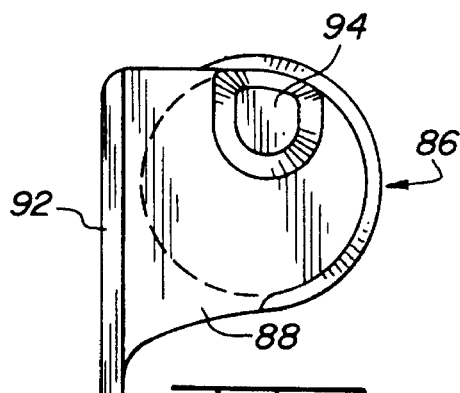
FIG. 18 is a top view illustrating a artificial mandibular fossa component according to the teachings of a third preferred embodiment of the present invention.
Figure 19:
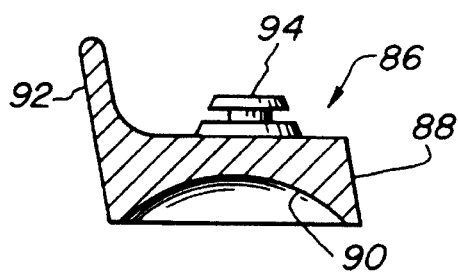
FIG. 19 is an end view illustrating the artificial mandibular fossa component shown in FIG. 18.
Figure 20:
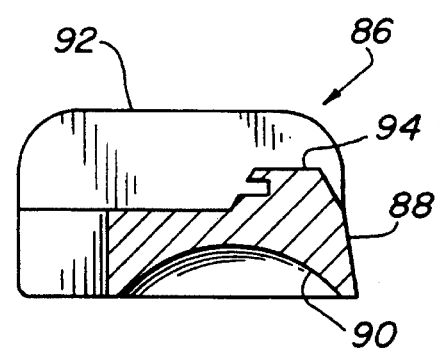
FIG. 20 is a side view illustrating the artificial mandibular fossa component shown in FIG. 18.

A further embodiment of artificial mandibular fossa component is shown now with reference to FIGS. 18, 19 and 20. The artificial mandibular fossa component 86 according to this embodiment includes a main body 88 which has an articular surface 90 with a concave surface of a second spherical radius greater by about 5%, and preferably greater by between about 5% and about 35%, than the first spherical radius of a corresponding articular surface of an artificial condyle component. The artificial mandibular fossa component 86 also includes a flange 92 which is disposed as an integral extension of the main body 88. It will be noted that in this embodiment, the flange 92 is disposed as a tapered extension which shares a boundary with the main body 88. The artificial mandibular fossa component 86 also includes a peg 94 which is operable for enhancing a secured relation with the natural mandibular fossa in which this feature is placed, due to its ability to provide an enhanced engagement surface for contacting an adhesive, as before.

It will be appreciated that the examples set forth in FIGS. 1–20 are meant to be illustrative of the varieties of artificial condyle component shapes and artificial mandibular fossa component shapes which may be constructed according to the present invention. It will further be appreciated that these components may be constructed of any of the materials previously discussed, or may be constructed from other suitable materials. It will further be appreciated that any of the above or other suitable configurations for artificial condyle components may be mated with any of the above or other suitable configurations for the artificial mandibular fossa component to produce a prosthetic device according to the present invention. In addition, it will be appreciated that the components of the prosthetic device of the present invention discussed above may be secured by suitable means for fastening the artificial condyle component to the ramus and means for fastening the artificial mandibular fossa component to the zygomatic arch, which may be the same or different, and which may include the use of any of the above types of surgical fasteners, including bone screws of a type well known to those skilled in the art, or may alternatively include other suitable selections of surgical fasteners.

In a method of the present invention, a surgical procedure is performed whereby the entire temporomandibular joint is replaced with a biocompatible prosthetic device 28 such as that described above. Firstly, one or more incisions are made in the skin along the ear and/or along one or more wrinkles of the neck, so as to minimize cosmetic distortion of the skin following surgery. This step is operable to expose the temporomandibular joint as may be necessary to accomplish the surgical procedure thereon.

In the second step of the method of the present invention, the masseter muscle is striped from its origin to expose the ramus 16. Following this, the disk is removed, if not absent at the time of surgery, from the interarticular region, thereby fully exposing the natural mandibular fossa and articular eminence of this joint.

In the next step of the method of the present invention, the articular surface of the condyle, such as that shown at 18 in FIG. 2, is resected to a preselected configuration. The preselected configuration is preferably suitable for allowing the subsequent attachment of an artificial condyle component, such as that shown in FIG. 3 at 30. A preferred mode of resection well known to those skilled in the art involves using a high speed burr to perform a planar condylectomy through the natural neck of the condyle 15. This is preferably performed at a suitable location below the articular surface 18 where the remaining bone stock will not interfere with the function of the artificial condyle component following installation. During this procedure, the pterygoid muscle is resected and may be retained for subsequent reattachment.

In the following step, at least a portion of the articular eminence of the temporal bone, such as that illustrated at 24 in FIG. 2, is flattened. This procedure is performed by means well known to those skilled in the art, such as through the use of a high speed burr, as before.

In the next step of the method, means for providing a substantially spherical concave articular surface for replacing the articular surface of the mandibular fossa is secured into the natural mandibular fossa 20 and attached to the zygomatic arch 38. Preferably, this involves attaching an artificial mandibular fossa component, such as that shown at 36 in FIG. 3, to the zygomatic arch 38. This includes positioning the artificial mandibular fossa component 36 in a preselected location adjacent to the zygomatic arch 38 so as to align a surface of the artificial mandibular fossa component 36 with the natural mandibular fossa 20. Preferably, this step includes aligning a flange of the artificial mandibular fossa component, such as that shown at 62 in FIGS. 8, 9 and 10, with an external surface of the zygomatic arch 38.

This procedure includes affixing the means for providing a substantially spherical concave articular surface, such as the artificial mandibular fossa component 36, to the zygomatic arch 38. In this step, bone cement is operable for enhancing a secured relation with the upper surface of the artificial mandibular fossa component 36, especially around a surface such as the tab 64 described in connection with FIGS. 8, 9 and 10. As such, the adhesive is being used to augment the natural mandibular fossa and stabilize the implant on the articular eminence.

In the next step of the method of the present invention, a plurality of apertures are created through the artificial mandibular fossa component 36 in a preselected configuration. The preselected configuration is preferably operable for enhancing a secured relation of the artificial mandibular fossa component 36 with the underlying zygomatic arch once the plurality of surgical fasteners are inserted therethrough. This preferably involves creating a minimum number of precisely located fastener openings upon the flange 62, depending upon the configuration of the zygomatic arch, so that each portion of the flange 62 may be successfully retained upon the zygomatic arch 38. Preferably, from two to four such fastener openings, and most preferably three such openings, are created by means well known to those skilled in the art, such as by conventional hand drilling, through the flange 62. The fastener openings may be created in a single diameter, or may be created in two or more diameters, for accepting fasteners of different diameters.

A plurality of pilot apertures are then created into the zygomatic arch 38 by means well known to those skilled in the art, such as by conventional drilling. The pilot apertures are created in a configuration corresponding to the fastener openings previously created within the artificial mandibular fossa component 36. As before, the pilot apertures may be created in a single diameter, or may be created in two or more diameters, for accepting fasteners of different diameters, when fastener openings of two or more sizes have been created within the flange 62. These pilot apertures are thus operable for accepting a plurality of surgical fasteners of the type previously described for enhancing a secured relation between the artificial mandibular fossa component 36 and the zygomatic arch 38.

As before, the pilot apertures are preferably created to a suitable depth within the zygomatic arch 38 that is substantially equal to the length of the surgical fastener being used, minus that portion of the length represented by the portion of the fastener head that is expected to protrude above the flange 62, minus the thickness of the flange 62. As before, the pilot apertures are preferably created at a diameter equal to the minor diameter of the fastener selected, that is, the diameter of the shaft portion of the fastener omitting that portion represented by the fastener threads.

In the next step of the method of the present invention, a plurality of surgical fasteners are threadably inserted through the plurality of apertures and pilot apertures into the zygomatic arch 38, and are suitably tightened against the flange 62, thereby engaging the artificial mandibular fossa component 36 with the zygomatic arch 38 in a substantially secured relation.

In the next step, the upper and lower teeth are substantially aligned in a normal bite relationship prior to securing the artificial condyle component 30. This allows the surgeon to manipulate the relative position of the artificial condyle component 30 to the artificial mandibular fossa component 36 so as to achieve an engagement that is most favorable for enhancing activity of the joint following the surgery which most nearly resembles the natural jaw movement. In this procedure, the upper and lower teeth are wired in a substantially aligned relation and the artificial condyle component 30 is manipulated and positioned for achieving the desired engagement between the respective convex articular surface 56 and the concave articular surface 60.

In the next step of the method of the present invention, means for providing a substantially spherical convex articular surface for replacing the articular surface of the condylar head is attached to the ramus 34. Preferably, this involves attaching an artificial condyle component, such as that shown at 30 in FIG. 3, to the ramus 34. This step includes positioning the condyle 56 of the artificial condyle component 30 flush with the concave articular surface of the artificial mandibular fossa component 36 and then the plate 48 is located adjacent to the ramus 16, so as to align a plurality of condylar fastener openings disposed thereupon, such as those shown at 50 in FIGS. 6 and 7, with a surface of the ramus 34, shown in FIG. 3.

A plurality of pilot apertures are then created into the ramus 34 by means well known to those skilled in the art, such as by conventional drilling. The pilot apertures are created in a configuration corresponding to the condylar fastener openings 50 disposed upon the artificial condyle component 30. The pilot apertures may be created in a single diameter, or may be created in two or more diameters, for accepting condyle fasteners 32 of different diameters. These pilot apertures are thus operable for accepting a plurality of surgical fasteners of the type previously described for enhancing a secured relation between the artificial condyle component 30 and the ramus 34.

The pilot apertures are preferably created to a suitable depth within the ramus 34 that is substantially equal to the length of the surgical fastener being used, minus that portion of the length represented by the portion of the fastener head that is expected to protrude above the plate 48 or plate countersink 52, minus the thickness of the plate 48. The pilot apertures are preferably created at a diameter equal to the minor diameter of the fastener selected, that is, the diameter of the shaft portion of the fastener omitting that portion represented by the fastener threads.

The means for fastening the means for providing a substantially spherical convex articular surface to the ramus 34 is then positioned to enhance an engaged relation between these two surfaces. Preferably, this involves fastening the artificial condyle component 30 to the ramus 34.

A plurality of surgical fasteners are then used to attach the artificial condyle component 30 to the ramus 34. Where the selection of surgical fasteners is a plurality of self-tapping bone screws of the type previously described, this is accomplished by threadably inserting the bone screws through the plurality of condylar fastener openings 50 and the pilot apertures previously described into the ramus 34 and are suitably tightened, thereby engaging the artificial condyle component 30 with the ramus 34 in a substantially secured relation. The wiring of the teeth can then be removed for an assessment of range of motion of the repaired joint.

Once joint motion is restored to create the desired motion, the method of the present invention may further include the reattachment of the pterygoid and masseter muscles to the artificial temporomandibular joint. In addition, the muscles may be reattached to the remaining bone stock, such as the neck of the ramus and the posterior/inferior border of the mandible, through methods well known to those skilled in the art, such as through the use of soft tissue anchors. In the final step of the present invention, the surgical procedure is concluded by closing the skin through methods well known to those skilled in the art.

While the above description discusses a preferred embodiment of the present invention, it will be understood that the description is exemplary in nature and is not intended to limit the scope of the invention. For example, the prosthetic device used in the present invention may include an artificial condyle component and an artificial mandibular fossa component of the types discussed above, or of other types which may be suitable for the particular purpose. The present invention will therefore be understood as suspectable to modification, alteration and variation by those skilled in the art without deviating from the scope and meaning of the following claims.

What is claimed is:

1. A biocompatible prosthetic device for the replacement of a temporomandibular joint having a mandible and a temporal bone, said biocompatible prosthetic device comprising:
   an artificial condyle component for fastening to the mandible, said artificial condyle component including a condylar head having an articular surface, said articular surface including a substantially spherical articular surface of a first spherical radius forming a substantial portion of the articular surface; and
   an artificial mandibular fossa component for fastening to the temporal bone, said artificial mandibular fossa component having an spherical articular surface of a second spherical radius greater than said first spherical radius, said artificial mandibular fossa component being operable to engage said condylar head in an articulating manner.

2. The biocompatible prosthetic device according to claim 1, wherein said spherical articular surface of said artificial condyle component is convex and said spherical articular surface of said artificial mandibular fossa component is concave.

3. The biocompatible prosthetic device according to claim 1, wherein said second spherical radius is at least about 5% greater than said first spherical radius.

4. The biocompatible prosthetic device according to claim 3, wherein said second spherical radius is between about 5% and 35% greater than said first spherical radius.

5. The biocompatible prosthetic device according to claim 1, wherein said artificial condyle component includes a plate attached to said condylar head.

6. The biocompatible prosthetic device according to claim 1, wherein said artificial condyle component includes a plurality of condylar fastener openings.

7. The biocompatible prosthetic device according to claim 1, wherein said artificial mandibular fossa component further comprises a flange integrally formed thereupon, said flange being operable to allow the formation of a plurality of fastener openings therethrough during replacement of the temporomandibular joint.

8. The biocompatible prosthetic device according to claim 1, wherein the temporal bone has a plurality of fastener openings, said biocompatible prosthetic device further comprising a plurality of fasteners being operable to traverse the plurality of fastener openings formed in the temporal bone.

9. The biocompatible prosthetic device according to claim 1, wherein said first spherical radius is at least about 0.200 inch.

10. The biocompatible prosthetic device according to claim 1, wherein said artificial condyle component includes a porous titanium coating being operable to contact the mandible.

11. A biocompatible prosthetic device for the replacement of a temporomandibular joint, said temporomandibular joint including a mandible having a condylar head with an articular surface and including a temporal bone with an articular surface, said biocompatible prosthetic device comprising:

means for providing a first articular surface for replacing the articular surface of the condylar head, said first articular surface including a substantially spherical articular surface of a first spherical radius forming a substantial portion of the first articular surface, said means for providing an articular surface being operable to be attached to the mandible; and means for providing a second substantially spherical articular surface of a second spherical radius greater than said first spherical radius for replacing the articular surface of the temporal bone, said means for providing a second substantially spherical articular surface being operable to engage said means for providing a first articular surface in an articulating manner, said means for providing a second substantially spherical articular surface being operable to be attached to the temporal bone.

12. The biocompatible prosthetic device according to claim 11, wherein said first substantial spherical articular surface is convex and said second substantial spherical articular surface is concave.

13. The biocompatible prosthetic device according to claim 11, wherein said means for providing a first substantially spherical articular surface includes an artificial condyle component having a condylar head.

14. The biocompatible prosthetic device according to claim 13, wherein said artificial condyle component includes a plate being operable to be attached to the mandible.

15. The biocompatible prosthetic device according to claim 13, wherein said artificial condyle component includes a plurality of condylar fastener openings.

16. The biocompatible prosthetic device according to claim 11, wherein said means for providing a second substantially spherical articular surface comprises an artificial mandibular fossa component.

17. The biocompatible prosthetic device according to claim 16, wherein said artificial mandibular fossa component includes a flange integrally formed thereupon, said flange being operable to allow the formation of a plurality of fastener openings therethrough during replacement of the temporomandibular joint.

18. The biocompatible prosthetic device according to claim 16, wherein said means for providing a first substantially spherical articular surface includes a plurality of fastener openings for fastening said means for providing a first substantially spherical articular surface to the mandible.

* * * * *